United States Patent [19]

Voss et al.

[11] E Patent Number: Re. 31,764

[45] Reissued Date of Patent: Dec. 11, 1984

[54] PHARMACEUTICALS HAVING DOTTED ACTIVE INGREDIENTS AND A METHOD AND APPARATUS FOR THE PREPARATION THEREOF

[75] Inventors: Gunther Voss, Diessen; Peter Gruber, Biberach, both of Fed. Rep. of Germany

[73] Assignee: Boehringer Ingelheim GmbH, Ingelheim am Rhein, Fed. Rep. of Germany

[21] Appl. No.: 433,848

[22] Filed: Oct. 12, 1982

Related U.S. Patent Documents

Reissue of:

[64] Patent No.: 4,322,449
Issued: Mar. 30, 1982
Appl. No.: 109,420
Filed: Jan. 3, 1980

U.S. Applications:

[63] Continuation-in-part of Ser. No. 94,238, Nov. 14, 1979, abandoned.

[30] Foreign Application Priority Data

Nov. 15, 1978 [DE] Fed. Rep. of Germany ..... 2948494

[51] Int. Cl.[3] ..... A61K 9/00

[52] U.S. Cl. ..... 427/3

[58] Field of Search ..... 427/3; 264/128, 109, 264/112, 113; 222/420–422; 424/16, 21

[56] References Cited

U.S. PATENT DOCUMENTS

| | | | |
|---|---|---|---|
| 2,836,291 | 5/1958 | Stroop | 424/21 |
| 3,007,848 | 11/1961 | Stroop | 424/16 |
| 4,126,503 | 11/1978 | Gardner | 424/16 |
| 4,139,589 | 2/1979 | Beringer | 264/132 |

*Primary Examiner*—Sam Silverberg
*Attorney, Agent, or Firm*—Hammond & Littell, Weissenberger & Muserlian

[57] ABSTRACT

A method for the preparation of pharmaceuticals which comprises using a piezoelectric dosing system to dot liquid, dissolved or suspended active substance onto a pharmaceutical carrier.

6 Claims, 5 Drawing Figures

PHARMACEUTICALS HAVING DOTTED ACTIVE INGREDIENTS AND A METHOD AND APPARATUS FOR THE PREPARATION THEREOF

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation-in-part of copending U.S. patent application Ser. No. 094,238 filed Nov. 14, 1979 now abandoned.

This invention relates to pharmaceuticals and a method and apparatus for the preparation thereof. More particularly, this invention relates to pharmaceuticals having dotted active ingredients and a method and apparatus for the preparation thereof.

BACKGROUND OF THE INVENTION

The pharmaceutical industry has in the last few years arrived at increasingly more effective active substances due to intensive research. Whereas most active substances developed in previous years were dosed in the multiple milligram range (conventional doses of about 20 to 150 mg per tablet), since then active substances have been invented whose dose per tablet is only about a few milligrams. Such active substances present difficulties in processing since the quantity of active substance becomes disproportionately small in relation to the remaining mass of the molding, i.e., the carrier. Consequently, sufficiently homogeneous distribution of the active substance in the entire molding cannot be readily obtained by mixing. For example, in an investigation of digoxin tablets to be found on the United States market, deviations of up to ±50% from the declared quantity of digoxin per tablet were established.

The active substance has hitherto had to be distributed homogeneously in the granulate, and during such distribution of low-dosage active substances, comprehensive safety precautions have been required, for example, to protect the operating personnel. Furthermore, comprehensive industrial operations such as mixing, granulation, trituration, or fine grinding have been unavoidably necessary. Moreover, in pressing tablets of low-dosage active substances, the dissolution rate and consequently the resorption capacity of the active substance in the body are influenced in a negative way by unavoidable sintering actions. In the preparation of tablets or coated-tablet cores with active substances of very low dosage, the exact dosing of these active substances is of special importance; however, this exact dosing requirement is often possible only to an insufficient degree with conventional processes.

DESCRIPTION OF THE INVENTION

Figure 1:
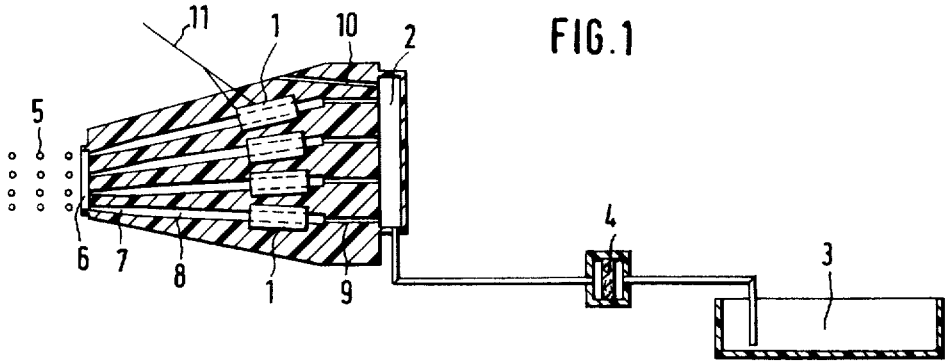
FIG. 1 represents a cross-section of one embodiment of the pharmaceutical dotting system of the invention.

It has now been found that an extremely precise dosing of active pharmaceutical ingredients onto pharmaceutical carriers can be achieved if the liquid, dissolved or suspended active substance is dotted onto the pharmaceutical carrier in a specific quantity in the form of discrete droplets of specific volume. The dotting is effected by, for example, means of tubular or plate-shaped piezoelectric dosing systems. However, the liquid, dissolved or suspended active substance can also be divided into discrete droplets of specific volume after application of a high pressure during passage through a narrow nozzle, whereby the individual droplets are successively charged electrically and are intermittently deflected electrostatically towards the pharmaceutical carriers.

A system suitable for dotting liquid, dissolved or suspended active substance onto the pharmaceutical carrier consists of, for example, one or an entire series of channels, whereby a tubular piezoelectric oscillator concentrically encases a section of each channel. Conductive layers, for example, silver layers or gold or nickel layers, on the faces of the tube-shaped piezoceramic oscillator, serve as electrodes to apply the electrical field.

The outlet openings of the channels are nozzle-shaped and are aligned so that each individual opening disperses, i.e., dots, a specific region of the pharmaceutical carrier with one or a specific number of droplets of specific volume of the liquid, dissolved or suspended active ingredient. The individual channels are connected on their feed side, for example, to a common distributor plate which is connected to a supply container and are provided, i.e., supplied, therefrom with a solution or suspension of active substance. (See, FIG. 1.)

Backflow of the solution or suspension in the nozzle channel is obstructed due to, for example, the nozzle channel being narrowed towards the outlet opening. As a result of the characteristic of piezoceramic oscillators to undergo an elastic deformation upon the application of a specific electrical field, a shock wave directed to the liquid arises in the piezoceramic tube-shaped oscillators. The pressure increase associated therewith leads to the ejection of very small quantities of active substance in lobe, or nodule, form from the outlet openings, these lobes, or nodules, of liquid assuming spherical form after leaving the outlet openings. The diameter of a channel is advantageously about 1 mm in its middle part, the individual channel being narrowed at its outlet opening. The diameter of the outlet opening is, for example, about 0.1 mm.

The supply container lies lower than the outlet openings, which gives rise to a vacuum system. Due to the height difference, a static vacuum arises in the channels. This static vacuum is overcompensated for a brief moment in the channels upon application of the electrical field, in conjunction with capillary action.

The capillary forces in the channels and in the outlet openings prevent the solution or suspension of active substance from running back.

The channel which is surrounded by the piezoelectric oscillator may be curved arbitrarily in front of or behind said oscillator. This form of arrangement, i.e., realization, serves for better adaptation of the active-substance dosing system to the spatial conditions of, for example, a tablet press. However, the channel may also be branched into two or more channels spatially after the piezoelectric oscillator, so that one piezoelectric oscillator supplies, i.e., acts upon, several channels with separate outlet openings.

The outlet openings may be, for example, holes in a glass or metal plate. If the channel consists of a glass capillary tube, the outlet opening may be formed by drawing out the glass tube at its end.

Another advantageous form of arrangement for dotting with liquid or suspended active substances consists of using plate-shaped planar transducers which work on the piezoelectric principle and which are preferably fitted concentrically in a distributor chamber above the entrance of the channels. Again, narrowed outlet openings are situated at the end of the channels. In a preferred form of arrangement, the piezoelectric plate lies in a distributor compartment horizontally concentrically to the channel leading away vertically. The piezoelectric plates lie in or on this compartment for receiving the liquid, dissolved or suspended active substance. Also, several channels may lead away from, i.e., be connected to, a common compartment which is connected, in turn, to a common liquid supply. Thus, a planar oscillator (piezoelectric plate) can also simultaneously generate a pressure wave in several channels connected to the same distributor compartment.

A further advantageous, constructively simplified arrangement comprises a planar oscillator with strong stroke in the distributor compartment and a channel which leads from the distributor compartment, the channel having situated at its end several nozzles optionally aligned variously in space or a nozzle rim. Due to such an arrangement a surface dotting of the pharmaceutical molding can be obtained with a single stroke generated by the piezoelectric oscillator. (See, FIGS. 2a, 2b and 2c.)

To direct the droplets generated by piezoelectric transducers to the desired surfaces of the pharmaceutical carrier, it is advantageous in many cases to charge said drops after they leave the outlet openings by the application of the electrical voltage, and to subsequently control their path by electrostatic deflection. This control may be effected with conventional means, for example, on the principle of cathode-ray deflection in a television tube.

The piezoceramic bodies may also be used as valves if the active substance solution or suspension is supplied with pressure to the oscillator or transducer which opens or closes according to the control. Upon selection, for example, a slit-shaped opening opens briefly in a channel containing liquid under pressure and the active ingredient material is delivered through said opening in drop form. The opening may be fashioned in the oscillator itself, which closes as a valve the space standing under pressure, or in the marginal zone between the oscillator and the material forming the walls of the channel. This operation is possible also in reverse, whereby upon selection the oscillator closes the space standing under pressure.

The drops necessary for dotting may also be generated by the so-called high-pressure process. In the high-pressure process, the active substance solution or suspension is forced under high pressure through one or more narrow nozzles. The high pressure is generated by, for example, a pump. Immediately after leaving the nozzle, the solution or suspension is divided into fine droplets of uniform size which are subsequently charged by a charging electrode. The electrically charged droplets are deflected electromagnetically or electrostatically to the desired points of the pharmaceutical carriers. (See, FIG. 3.)

The droplets generated by the above-described high-pressure system have a diameter of, for example, 20 μm. These droplets can, if desired, be further divided by the application of a strong electrical field of, for example, about 500 to 1000 volts. These finer charged droplets may in addition be used for the directed dotting of the pressing tools due to electrostatic deflection.

The active substance dosing system preferably used, also called micropumping system, works with tubular or plate-shaped piezoelectric oscillators. Upon the application of a voltage pulse of, for example, 100 volts and a pulse duration of 20 microseconds, droplets are ejected at a velocity of about 4 m/sec and with a very constant droplet weight of, for example, 0.8 μg (0.0008 mg). Depending on the electronic control, the drop frequency may be between about 1 and 50,000 drops per second, preferably about 3,000 drops per second.

The dosing may be controlled by one or more of the following parameters:

(a) the diameter of the outlet opening of the nozzle channels;
(b) the voltage applied to the piezoelectric oscillator;
(c) the droplet frequency;
(d) the number of nozzle channels;
(e) the stroke intensity of the tubular or planar oscillator used;
(f) the active substance concentration of the solution or suspension; and
(g) the number of dots of active substance per pharmaceutical carrier.

Figure 2A:
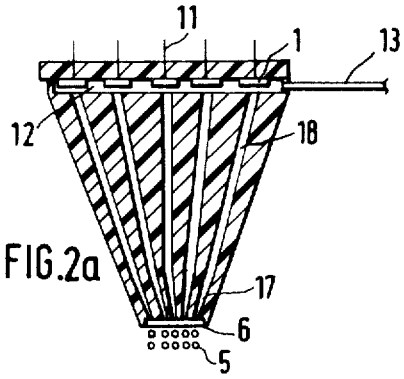
FIGS. 2a, 2b and 2c represent cross-sections of different dotting heads with planar transducers.
Figure 2B:
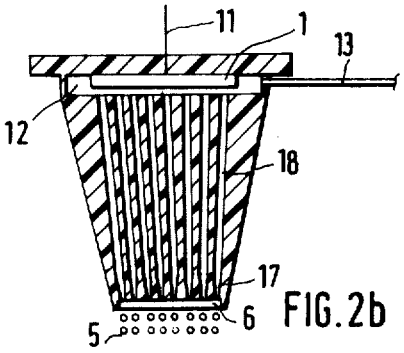
Figure 2C:
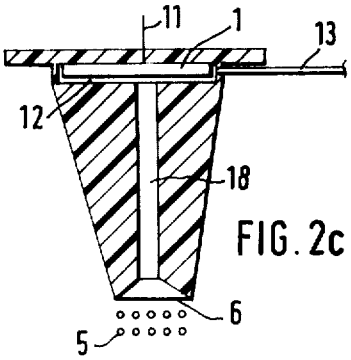
Figure 3:
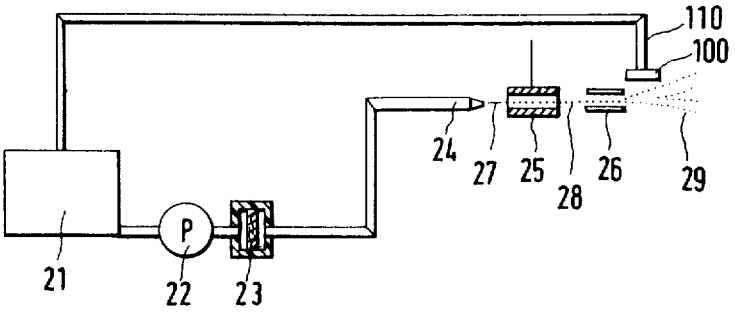
FIG. 3 represents a cross-section of a high-pressure dotting system.

FIGS. 1 to 3 are intended to illustrate schematically and in an exemplary manner a few possible devices for dotting pharmaceutical carriers with liquid, dissolved or suspended active substances.

FIG. 1 shows schematically in cross-section a dotting system with piezoelectric transducers (1) which each encase a nozzle channel (8). The nozzle channel terminates in a narrowing (7), and the individual narrowings (7) are present at corresponding openings of an outlet nozzle plate (6), whereby the nozzles formed by the narrowings (7) and the openings of the outlet plate (6) deliver droplets of liquid (5) when the device is actuated. The nozzle channel (8) is connected via a narrowed liquid channel (9) to a liquid distributor compartment (2). The distributor compartment (2) has a vent channel (10), and the distributor compartment is connected via a filter plate (4) to a liquid supply container (3). The electrical control of the piezoelectric transducers is effected via contacts (11).

FIGS. 2a, 2b, and 2c show cross-sections of variously constructed dotting heads with planar transducers working on the piezoelectric principle. Here, planar piezoelectric transducers (1) have contact (11) for electrical control. The planar piezoelectric transducers lie in a liquid distributor compartment (12) which is connected via the liquid line (13) to a supply container. One or more nozzle channels (18), whose narrowings (17) terminate at an outlet nozzle plate (6), lead away from the distributor compartment (12). Liquid droplets (5) are released from the nozzle plate (6).

FIG. 3 is a schematic cross-section of a so-called high-pressure dotting system. From a liquid supply container (21) liquid is pressed by means of a pump (22) through a filter (23) into a nozzle (24). A liquid jet (27) released at the nozzle (24) is decomposed, i.e., broken, into drops (28) which are charged electrically by a drop charging ring (25) and are deflected by means of a deflector plate (26) in an electrical field. The deflected liquid drops (29) dot the pharmaceutical carriers. The remaining, i.e., undeflected, drops (29) are drawn up by a suction electrode (100) and collected and are returned to the container (21) via line (110).

The following possibilities arise for the dosed application of active substances on pharmaceutical carriers: in the preparation of tablets a carrier granulate is used which is introduced volumetrically in a conventional way into the molds via the granulate filling shoe. Immediately after the carrier granulate leaves the filling station, the active substance liquid is dotted onto the granulate. If, in so doing, a dosing system (see FIG. 2c) with a planar oscillator of strong stroke and having a number of nozzle openings adapted to the form and size of the surface of the mold, is used, then the desired quantity of active substance can be dotted in a distributed manner, for example, by a single stroke.

A uniform dotting of the surface of the granulate situated in the mold may be effected also due to the fact that the micropumps arranged in a row are controlled electronically so that only those micropumps deliver active substance liquid which are situated just above the passing granulate surface.

The above-described dotting systems may, however, also be attached at the point in the tablet press at which the finished molding is ready for ejection from the mold, that is, the liquid active substance is dotted directly onto the finished molding. Finally, a dotting of the active substance carrier by these two dotting systems may also be effected by moving the finished placebo active substance carriers past the above-mentioned dosing systems outside the range of the tableting machines. In other words, the moldings are separated and moved in series past the dotting system, the dotting operations being started by, for example, photocells. The above-mentioned dosing systems may, of course, also be attached to capsule-filling machines.

With flat, concave, or convex active substance carriers, for example, oblates, the individual micropumps can be controlled so that a geometrical pattern arises thereby on the face of the active substance carrier. If the active substance solution is colored, a coding or labelling on the carrier surface may be obtained without contact, simultaneously with the dosing of the active substance. Since the dosing operation proceeds without contact, the actual geometry of the surface of the active substance carrier plays no part and this surface may be shaped, for example, convexly or concavely or also completely irregularly. The use of a colored active substance solution also offers an additional advantage: the completeness of the dosing can be checked by means of an automatic reading unit (for example, an optical scanner).

The delivered droplets may, of course, also be detected by an electronic counter. The active substance is generally dissolved in physiologically harmless solvents such as water, glycerine, glycol or alcohols such as ethanol. The active substance may also be ground finely in a ball mill and suspended in a suspension agent.

With the above-described dotting systems, droplets of the active substance solution or suspension of exactly the same size and the same weight are transferred onto the active substance carrier. In so doing, the number of droplets applied per dotting action can be limited precisely by an electronic control, if desired of each individual nozzle, whereby with a given content of active substance, for example, in the solution or suspension, an extremely accurate dosing is made possible. The individual dotting actions are, of course, coupled to the speed of the tableting machine. To generate corresponding signals which are input to the control, photocells scanning the mold, for example, are used.

A very advantageous effect for the preparation of certain pharmaceutical forms is provided by the fact that due to a directed dotting, especially with flat active substance carriers, individual zones can be dosed with specific concentrations of pharmaceutical, whereby these concentrations may also differ from one another from carrier to carrier in definite ratios.

The process of dosed dotting of pharmaceutical carriers opens up the possibility of exact dosing of active substance, as it has not been possible to achieve with the conventional methods. If placebo tablets or coated tablets are used, these placebo active substance carriers can be made of cheap carriers rationally and consequently economically in large quantities. Instead of placebo tablets or coated tablets, flat pharmaceutical carriers such as oblates, gelatine plates or carriers of absorbent substances can also be used. According to the conventional dosing methods; these carriers cannot be loaded exactly in an economical manner. If the above-mentioned carriers are adopted, expensive operations such as mixing, granulation, drying, and pressing of granulates can be omitted. A substantial reduction of the machine requirement and of the production areas is consequently possible and the finished pharmaceutical can be produced more cheaply.

The following examples are intended to illustrate the invention and are not to be construed as limiting the invention thereto.

EXAMPLES

Example 1

| Tablets | |
|---|---|
| Component | Weight (mg) |
| Lactose | 75 |
| Corn starch | 125 |
| Secondary calcium phosphate | 40 |
| Soluble starch | 3 |
| Magnesium stearate | 4 |
| Colloidal silicic acid | 3 |
| | 250 |

A part of the above-described mixture was kneaded intensively with an aqueous solution of the soluble starch and was granulated conventionally by means of a screen. The granulate was mixed with the remaining excipients and was pressed to tablets each weighing 250 mg. By means of a planar oscillator which was attached in a compartment above a channel provided at its other end with a nozzle rim, a dose of 0.06 mg of the (dissolved) active substance (e.g., clonidine hydrochloride in water/ethanol) was dotted onto these tablets at the moment of outlet from the press compartment. When the active substance was determined on 20 individual tablets all the values lay within the tolerance of the method analysis (±0.5%).

EXAMPLE 2

An edible pharmaceutical carrier was printed with a dosing system equipped with 12 tubular piezoelectric oscillators. The label which comprised the name of the preparation, the dosage, and the taking time, was composed of 250 dots (one letter was formed from about 20 dots). The weight of a drop was about $1\gamma=0.001$ mg. The concentration of the active substance ink was adjusted so that the label contained exactly $100\gamma=0.1$ mg of active substance. The dosing system worked at a rate of 300 letters per second, and the active substance drop frequency was 3,000 dots per second.

EXAMPLE 3

Nine millimeter placebo tablets prepared from lactose, corn starch, and microcrystalline cellulose were conveyed at a constant speed of 1 m per second past a dosing head on separating apparatus. The dosing head consisted of a strong planar piezoelectric oscillator. One hundred nozzle channels were arranged in a circle so that they dotted the entire surface of the tablet uniformly. The dosing operation was completed in 1 millisecond. During this time the planar piezoelectric oscillator had executed 5 strokes and a total of 5 mg of a 20% active substance suspension was delivered.

When the active substance was determined on 20 individual tablets, all the values lay within the tolerance of the method of analysis ($\pm 1\%$). About 200,000 tablets per hour can be dotted with the active substance suspension.

While the present invention has been illustrated with the aid of certain specific embodiments thereof, it will be readily apparent to others skilled in the art that the invention is not limited to these particular embodiments, and that various changes and modifications may be made without departing from the spirit of the inventions or the scope of the appended claims.

We claim:

1. A method for the preparation of solid pharmaceuticals, which comprises dotting liquid, dissolved or suspended active substance in a specific quantity in the form of discrete droplets of specific volume onto a pharmaceutical carrier granulate in a mold before the pharmaceutical carrier granulate is pressed into tablets or cores.

2. A method for the preparation of solid pharmaceuticals, which comprises dotting liquid, dissolved or suspended active substance in a specific quantity in the form of discrete droplets of specific volume onto pharmaceutical carrier in the powder bed of an unsealed capsule in a capsule filling machine.

3. The method of claims 1, or 2, wherein the dotting is effected by means of piezoelectric dosing systems.

4. The method of claim 3, wherein a piezoelectric transducer wholly or partly encloses an outlet opening and the dotting is effected in such a way that the release of droplets from a liquid standing under pressure is achieved by the controlled opening of the outlet opening.

5. The method of claims 1, or 2, wherein the liquid, dissolved or suspended active ingredient is broken up under high pressure during passage through a nozzle into discrete droplets of specific volume and the individual droplets are successively charged electrically and intermittently deflected electromagnetically to the desired points of the pharmaceutical carrier.

6. The method of claims 1, or 2, wherein pharmaceutical carriers are dotted in series next to one another with the liquid, dissolved or suspended active substance.

[7. The method of claims 1, or 2, wherein the liquid, dissolved or suspended active substance is dotted onto a flat pharmaceutical carrier in desired geometrical distributions.]

[8. The method of claims 1, or 2, wherein the liquid, dissolved or suspended active substance is dotted onto specific zones of a flat pharmaceutical carrier in doses different from one another.]

[9. The method of claims 1, wherein the liquid, dissolved or suspended active substance is mixed with a dyestuff and is dotted onto a pharmaceutical carrier to form a coding or letter characters.]

* * * * *